United States Patent
Patel et al.

(10) Patent No.: US 12,343,427 B1
(45) Date of Patent: Jul. 1, 2025

(54) STABLE INTRAVENOUS DILTIAZEM HYDROCHLORIDE FORMULATION AND USE THEREOF

(71) Applicant: Nivagen Pharmaceuticals, Inc., Sacramento, CA (US)

(72) Inventors: Niravbhai Jayantibhai Patel, Sacramento, CA (US); Robert Miller, Sacramento, CA (US); Maheshkumar Kalubhai Bhalaria, Sacramento, CA (US); Mahesh Sadashiv Khade, Sacramento, CA (US); Rucha Abhijit Kelekar, Sacramento, CA (US); Dasaradhi Lakkaraju, Sacramento, CA (US); Jay Shukla, Sacramento, CA (US)

(73) Assignee: Nivagen Pharmaceuticals, Inc., Sacramento, CA (US)

( * ) Notice: Subject to any disclaimer, the term of this patent is extended or adjusted under 35 U.S.C. 154(b) by 0 days.

(21) Appl. No.: 18/643,088

(22) Filed: Apr. 23, 2024

(51) Int. Cl.
*A61K 9/08* (2006.01)
*A61J 1/10* (2006.01)
*A61K 9/00* (2006.01)
*A61K 31/554* (2006.01)
*A61K 47/02* (2006.01)
*A61K 47/12* (2006.01)

(52) U.S. Cl.
CPC .............. *A61K 9/08* (2013.01); *A61J 1/10* (2013.01); *A61K 9/0019* (2013.01); *A61K 31/554* (2013.01); *A61K 47/02* (2013.01); *A61K 47/12* (2013.01)

(58) Field of Classification Search
CPC .............................. A61K 9/0019; A61K 9/08
See application file for complete search history.

(56) References Cited

U.S. PATENT DOCUMENTS

| 11,241,379 | B2 * | 2/2022 | Kumar | A61K 47/10 |
| 2004/0039366 | A1 * | 2/2004 | MacLeod | A61K 9/0019 604/82 |
| 2008/0108685 | A1 * | 5/2008 | Sacher | A61P 31/12 514/401 |

* cited by examiner

*Primary Examiner* — James W Rogers
(74) *Attorney, Agent, or Firm* — Ted Whitlock Registered Patent Attorney. PA; Ted Whitlock

(57) ABSTRACT

A ready-to-use intravenous (IV) diltiazem composition that can be stored for extended periods.

12 Claims, 5 Drawing Sheets

STABLE INTRAVENOUS DILTIAZEM HYDROCHLORIDE FORMULATION AND USE THEREOF

BACKGROUND OF THE INVENTION

The subject invention addresses the clinical need for a ready-to-use intravenous (IV) diltiazem composition for injection that can be stored for extended periods.

Diltiazem hydrochloride (referred to herein as "diltiazem hydrochloride," "diltiazem HCl," or just "diltiazem") is useful for temporary control of rapid ventricular rate in atrial fibrillation or atrial flutter, providing rapid conversion of paroxysmal supraventricular tachycardias (PSVT) to sinus rhythm. Injectable diltiazem HCL solutions are frequently used in emergency departments, operating rooms, and intensive care units to treat atrial fibrillation/flutter (AFF).

Currently, a drug product containing diltiazem is commercially available under the generic name of Diltiazem Hydrochloride Injection, and is provided as 5 mg/ml concentrations, in 5 mL, 10 mL and 25 ml glass vials (25 mg/5 ml, 50 mg/10 ml and 125 mg/25 mL, respectively). These marketed diltiazem vials contain 50 mg/ml of sorbitol to improve chemical stability. These concentrated diltiazem solutions must be diluted prior to clinical use for continuous intravenous infusion, typically in 5% dextrose or 0.9% sodium chloride solutions or 5% dextrose and 0.45% sodium chloride injection.

Due to physicochemical instability of the diluted diltiazem solutions, the package labeling specifies that the diluted diltiazem injectable solution should be discarded within 24 hours of preparation. These labeling instructions for diluted preparations of diltiazem apply regardless of whether they are stored at room temperature 15° to 30° C. (59° to 86° F.) or under refrigeration 2° to 8° C. (36° to 46° F.). This instability and short shelf-life of the diltiazem preparations necessitates frequent preparation of diluted diltiazem solutions by clinical staff.

There are several disadvantages associated with the dilution required for currently marketed diltiazem vials, including:

1. Microbial contamination risk—Each dilution preparation introduces the potential for introduction of contaminating microorganisms into the diltiazem solution. While the concentrate vials are sterile, the dilution process usually relies on aseptic technique rather than true sterility.
2. Calculation errors-Manually calculating and performing the dilutions leaves room for human error in arriving at the final concentrations, potentially leading to improper dosing of diltiazem.

For these reasons, among others understood in the art, a ready-to-use "premixed" IV solution of diltiazem, which can avoid the need for frequent on-site dilution prior to patient administration can be advantageous, reducing risk of contamination, calculation errors, and adverse reactions.

Moreover, a ready-to-use composition that is stable when stored for extended periods, e.g., having stability and storage capability for more than 24 hours, and up to one month under normal conditions (room temperature) or longer (up to 12-24 months under refrigeration) can reduce costs and also contribute to improved safety, accuracy and consistency of dosing, and convenience, compared to the currently marketed concentrate.

These and other unexpected advantages are achieved by the claimed composition and its use.

BRIEF SUMMARY OF THE INVENTION

The subject invention concerns diltiazem solutions, specifically, solutions comprising diltiazem hydrochloride below concentrations of 5 mg/ml that remain stable for periods up to 12-24 months when stored under refrigeration conditions and remain stable for at least one month at room temperature, without the presence or addition of a stabilizer, such as a stabilizing sugar, e.g., sorbitol or dextrose.

At a concentration in the range of 0.5 to about 2.0 mg/ml, and preferably at a concentration of about 1.0 mg/mL, a diltiazem solution of the invention can avoid the need to be diluted immediately prior to use. Preferably, the diltiazem solutions of the invention are provided at about 1 mg/mL final concentration, packaged in conventional flexible sterile containers, such as 100 mL, 125 mL, 250 mL, 500 mL, or 1 Liter flexible polymeric bags/glass or plastic vials that are commonly used in the pharmaceutical industry for intravenous preparations. In one preferred embodiment, the flexible bag is translucent or transparent, and can include an outer opaque sleeve or cover to minimize exposure of the solution to incident light.

In one embodiment, a diltiazem composition according to the subject invention is a ready-to-administer diltiazem composition, comprising:
  an aqueous diltiazem HCL solution comprising a buffer and a pharmaceutically acceptable salt as a tonicity agent. The pharmaceutically acceptable salt can be a sodium salt or a chloride salt, such as NaCl. The buffer can be a citrate buffer comprising one or more citrate compounds, e.g., citric acid monohydrate, sodium citrate dihydrate, or both in combination, or Acetate buffer.

In one preferred embodiment, the ready-to-administer solution comprises about 1.0 mg/ml diltiazem HCL and has a pH range between 3.4 and 4.4. A composition of the invention comprises at least 95% of the diltiazem after six months storage under refrigeration, meaning that the refrigeration-stored composition comprises less than 5% desacetyl diltiazem and other total degradation products after storage for six months under refrigerated conditions.

In one embodiment of the invention, the composition is a sterile, ready-to-administer, packaged diltiazem composition, comprising:
  a first container filled with a sterile, ready-to-administer aqueous solution comprising between 0.5 mg/ml and 2.0 mg/ml diltiazem, at least one buffering agent and at least one tonicity agent at a concentration between about 0.8% (w/w) and 1.0% (w/w), said solution having a pH of between 3.4 and 4.4, and wherein the container is enclosed within a second opaque container, e.g., a sleeve or cover, which minimizes exposure of the solution within the first container to incident light
wherein the sterile, ready-to-administer, packaged diltiazem composition after storage at about 5° C. (±3° C.), for at least three months, comprises at least about 95% diltiazem as determined by high-pressure liquid chromatography (HPLC).

In one embodiment, the invention is a sterile, antioxidant-free aqueous diltiazem solution packaged in a flexible plastic container within a sealed over-wrap pouch, the diltiazem solution comprising between about 0.5 and 1.5 mg/ml of diltiazem HCl, a tonicity adjusting agent such that the solution has an osmolality between about 260 and 320 mosm/kg, a pH between about 3.4 to 4.4, wherein, after storage at about 5° C. for more than six months and up to 24 months, the solution remains clear and colorless and comprises at least 0.9 mg/ml diltiazem.

In yet another embodiment of the invention, there is provided a ready-to-administer diltiazem composition, comprising:
  an aqueous solution having a pH range of between 3.4 and 4.4, comprising between 0.05 wt. % and 0.1 wt. % diltiazem HCl, one or more buffering agent, and one or more pharmaceutically acceptable salt as a tonicity adjusting agent;
  wherein the composition comprises less than 5% desacetyl diltiazem and other diltiazem degradation products after storage over at least three months under refrigeration.

The subject invention includes a stable, injectable diltiazem composition, comprising:
  about 1 mg/ml diltiazem HCL as an active pharmaceutical ingredient;
  about 0.4 mg/ml or less of a buffer for maintenance of pH; and
  a pharmaceutically acceptable salt as a tonicity agent;
wherein the composition has a pH of about 2.5 to about 5.0;
wherein the composition is free of a sugar; and
wherein the composition is free of a sugar alcohol.

The buffer used in a composition described herein can be a citrate buffer, and is preferably a buffer system comprising citric acid monohydrate and tri-sodium citrate dihydrate. A preferred buffer system comprises about 0.15 mg/ml citric acid monohydrate and about 0.12 mg/mL tri-sodium citrate dihydrate.

The pharmaceutically acceptable salt used in a composition of the invention can be a sodium salt or a chloride salt, such as sodium chloride, and is preferably provided at a concentration of about 0.8 wt % to about 1.0 wt % of the composition. A preferred concentration of sodium chloride used in a composition of the invention is 0.9 wt %.

Advantageously, a composition of the invention is stable for at least one month at room temperature, compared to currently available diluted concentrates which are required to be discarded within 24 hours of preparation. At refrigerated temperatures, a composition of the invention is stable and can be stored for later use for up to 24 months. A composition of the invention is stable for at least six months, and more preferably is stable between about 12 months to about 24 months.

Stability of a composition of the invention is established by assay, e.g., HPLC assay, wherein a known degradant, such as desacetyl diltiazem HCL, is ≤5.0% of the composition at 24 hours after storage at room temperature, or at 6 months, 12 months, or 24 months after storage under refrigerated conditions. A preferred stable composition comprises ≤5.0% of all known impurities and degradants at 24 hours after storage at room temperature, or at 6 months, 12 months, or 24 months after storage under refrigerated conditions. In other words, at 24 hours after storage at room temperature, or at 6 months, 12 months, or 24 months after storage under refrigerated conditions, a composition of the invention comprises at least 95% of the active pharmaceutical ingredient, diltiazem.

A composition of the subject invention is free of a sugar, e.g., dextrose, and is free of a sugar alcohol, e.g., sorbitol. By being free of sugar or sugar alcohol, the composition of the invention can advantageously reduce the risk of hyperglycemia in a patient administered the composition.

A preferred composition of the invention has a pH of about 3.9. An acceptable range of pH for the subject composition can be between about 2.5 and about 5.0, preferably within a range of about 3.4 to about 4.4.

In a preferred embodiment, a composition of the subject invention is provided as a packaged, ready-to-administer stable injectable diltiazem composition. Preferably, the composition is packaged in a flexible, pharmaceutically acceptable bag, as is known in the art. For example, a preferred material used for a pharmaceutically acceptable bag is polyolefin.

Diltiazem HCL can be slightly light-sensitive. Accordingly, one preferred embodiment can include an opaque secondary outer sleeve or cover over the flexible bag to protect the composition from incident light and water loss considering the bag as a semi-permeable container. In a more preferred embodiment, the secondary outer sleeve or cover can also have the property of being capable of blocking or absorbing oxygen so that oxygen does not reach the contents (the composition) stored within the primary container, i.e., the pharmaceutically acceptable bag.

Preferably, use of the composition of the invention, being free of a sugar or a sugar alcohol as a stabilizer or preservative, can reduce the risk of hyperglycemic condition in a patient following administration to a patient in need thereof.

Use of a composition of the invention, including use of the composition as a ready-to-administer composition provided within a flexible bag, can reduce the risk of error in preparation resulting from preparation of diltiazem injectable solution by dilution of a 5 mg/ml concentrate composition to a 1 mg/ml concentration immediately prior to use.

Use of a composition of the invention provided in a flexible, pharmaceutically acceptable bag having an opaque secondary outer sleeve or cover over the flexible bag, can further increasing the stability of the composition, providing stability of the composition for at least 24 hours and up to one month at room temperature and for at least about six months to about 12-24 months under refrigeration.

DETAILED DESCRIPTION OF THE INVENTION

Figure 1:
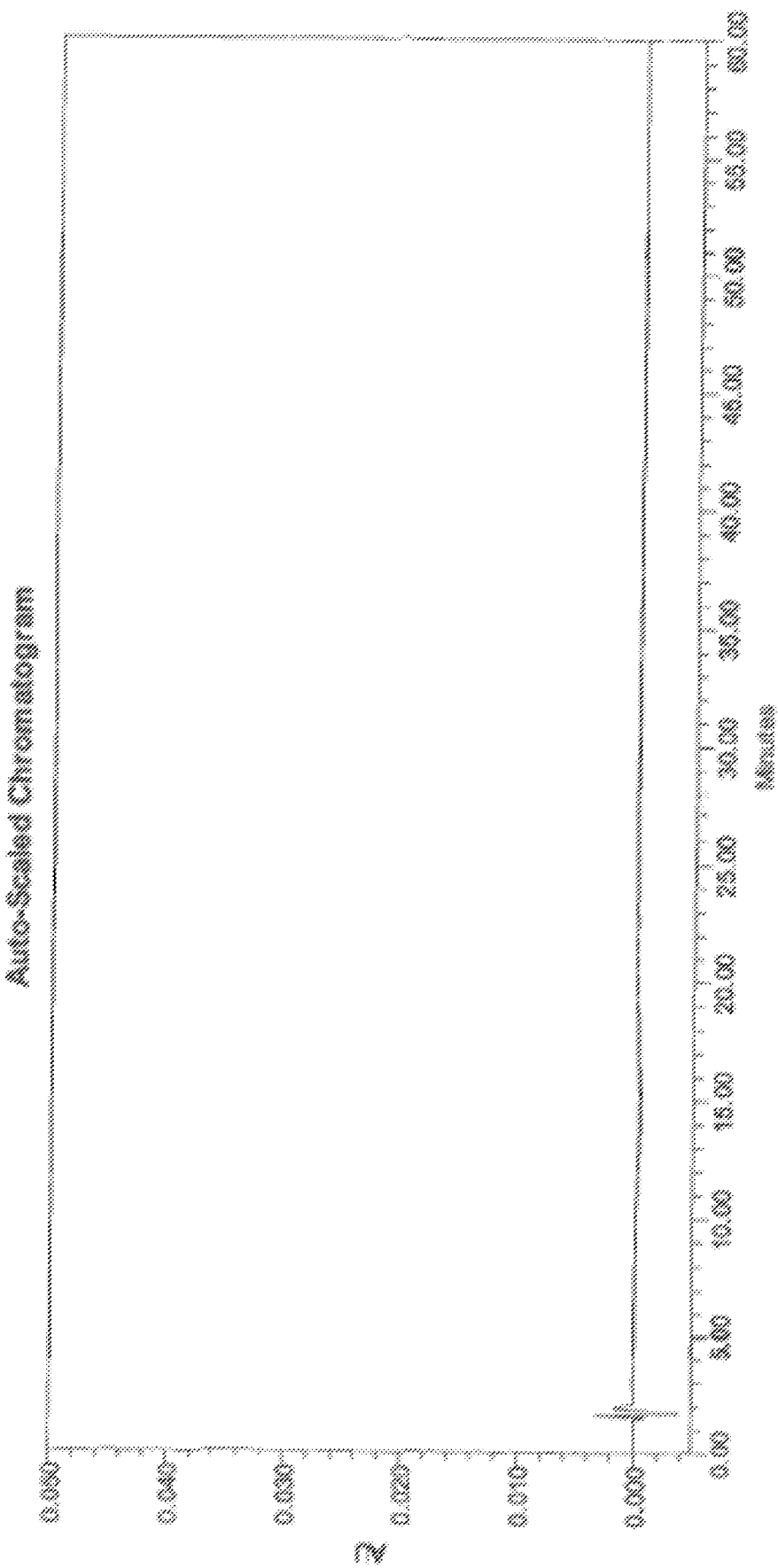
FIG. 1 shows a Blank Chromatogram, which is a High-Performance Liquid Chromatography (HPLC) chromatogram of blank sample, containing solvent, without drug.

The subject invention comprises a dilute, buffered solution comprising diltiazem hydrochloride, which is stable for at least one month at room temperature, and can be stable up to 24 months when stored under refrigeration.

Formulation of Composition: A composition of the invention is a ready-to-administer diltiazem HCl solution having a formulation as shown in Table 1.

TABLE 1

Diltiazem Hydrochloride (1 mg/mL) in 0.9% Sodium Chloride Injection

| Ingredients | Function | Quantity (mg/ml) | % w/v | Quantity/125 mL | Quantity/250 ml |
|---|---|---|---|---|---|
| Diltiazem HCl | API | 1.0 | 0.1% | 125.0 | 250.0 |
| Sodium Chloride | Tonicity Adjusting Agent | 9.0 | 0.9% | 1125.00 | 2250.0 |
| Citric acid monohydrate | Buffer | 0.15 | 0.015% | 18.75 | 37.5 |
| Sodium citrate dihydrate | Buffer | 0.12 | 0.012% | 15.0 | 30.0 |
| Sodium hydroxide | pH Adjuster | q.s. to adjust pH | q.s. to adjust pH | q.s. to adjust pH | q.s. to adjust pH |
| Hydrochloric acid | pH Adjuster | q.s. to adjust pH | q.s. to adjust pH | q.s. to adjust pH | q.s. to adjust pH |
| Water for Injection | Solvent | q.s. to 1.0 mL | q.s. to 100 % | q.s. to 125 mL | q.s. to 250 ml |

Typically, in the clinical use of diltiazem hydrochloride to treat atrial fibrillation/flutter (AFF), 5 mg/ml of diltiazem HCl (concentrate) provided in 5 mL or 10 mL or 25 ml vials, is diluted by adding the concentrate to a dextrose solution or sodium chloride intravenous (I.V.) solution, such that the final strength of the diltiazem HCL administered to the patient is about 1 mg/ml. Specific concentrations exemplified include 125 mg of diltiazem HCL added to 125 ml of solution and 250 mg diltiazem HCL added to 250 ml of solution. This means that five 5-ml vials of the 5 mg/mL concentrate needs to be added to a 100 ml bag of I.V. solution, or five 10 ml vials of 5 mg/mL concentrate needs to be added to a 200 ml bag of I.V. solution or one 25 mL vial of 5 mg/ml concentrate needs to be added to a 100 ml bag of I.V. solution. These correspond to quantities commonly used in clinical practice for continuous intravenous infusion.

In addition to diltiazem hydrochloride as the active pharmaceutical ingredient (API), the solutions according to the subject invention comprise water for injection and a tonicity adjusting agent to achieve isotonicity. The preferred tonicity adjusting agent is sodium chloride, added in quantities sufficient to provide osmolality between 260-320 mOsm/kg. Typically, the amount of sodium chloride used to obtain this desired tonicity is between 8-10 mg/ml, and more specifically around 9 mg/ml (a 0.9% w/v solution).

Unlike certain discontinued diluted formulations of injectable diltiazem HCL that contain dextrose, a composition of the subject invention specifically excludes dextrose. The absence of dextrose in the pharmaceutical composition of the invention can advantageously avoid risks of hyperglycemia caused by administration of a composition that includes dextrose or other sugars or sugar alcohol. Using sodium chloride as the sole tonicity agent can be beneficial for stability and can avoid glucose-related adverse effects. Accordingly, a diltiazem HCL composition of the subject invention is free of sugar, e.g., dextrose, and sugar alcohol, e.g., sorbitol, and specifically excludes dextrose and sorbitol.

Stability of the pH of a composition of the invention is achieved using a suitable buffer system to prevent pH fluctuation and minimize changes to the pH of the solution over time. One preferred buffering agent used for the subject composition is a citrate buffer or acetate buffer provided at about 0.002% to about 0.03% w/v of the composition. Buffer systems, e.g., combinations of two or more buffering agents can also be used. For example, a preferred combination of citrate buffers comprises a combination of citric acid monohydrate and sodium citrate dihydrate. Total concentrations of these citrate buffering agents typically do not need to exceed 0.03% w/v. For example, a preferred composition of the subject invention comprises about 0.015% w/v citric acid monohydrate and about 0.012% w/v sodium citrate dihydrate.

A preferred pH range of a composition of the invention is about 2.5-5.0, and has a more preferred pH range of about 3.4-4.4. Hydrochloric acid and sodium hydroxide can be used as needed to adjust the pH to a final preferred value of about 3.9.

Packaging

A diltiazem solution according to the subject invention aseptically filled into a sterile flexible plastic bag or container as described herein can have a shelf-life stability of at least one month at room temperature, and about 12 to 24 months under refrigerated conditions. A conventional material used in sterilizable, flexible plastic bags acceptable for use with injectable pharmaceuticals is polyolefin. Other materials known in the art or developed for future use can also be used.

Bags containing a diltiazem composition of the invention, e.g., polyolefin bags which are transparent or translucent, can be enclosed in a secondary, opaque overwrap or outer covering or pouch to protect the diltiazem composition from light exposure. In one preferred embodiment, the secondary, opaque overwrap or outer covering or pouch can block or absorb oxygen. The secondary, opaque overwrap or outer covering or pouch can therefore be useful to protect the diltiazem composition from environmental conditions, including exposure to oxygen or light, that can degrade the active pharmaceutical ingredient, such as diltiazem.

The described flexible plastic bags, water vapor/gas barrier secondary pouches, and aseptic filling processes are employed to produce shelf-stable diltiazem IV solutions that maintain potency when stored at refrigeration temperature for up to two years. This enhances convenience for the user by avoiding the need for on-site dilution of more concentrated diltiazem solutions, e.g., 5 mg/ml concentrations, stored in vials and which can include a stabilizer, such as dextrose, that can be disadvantageous.

For testing the degradation of diltiazem over time, an assay for diltiazem or its degradation products, can employ a high-performance (or high-pressure) liquid chromatography (HPLC) process. An exemplary HPLC process for conducting diltiazem or diltiazem degradation products is provided below. The diluent was injected at the beginning of the run as Blank and had no peaks that interfered with Diltiazem at around 14 minutes as shown in FIG. 1.

Figure 2:
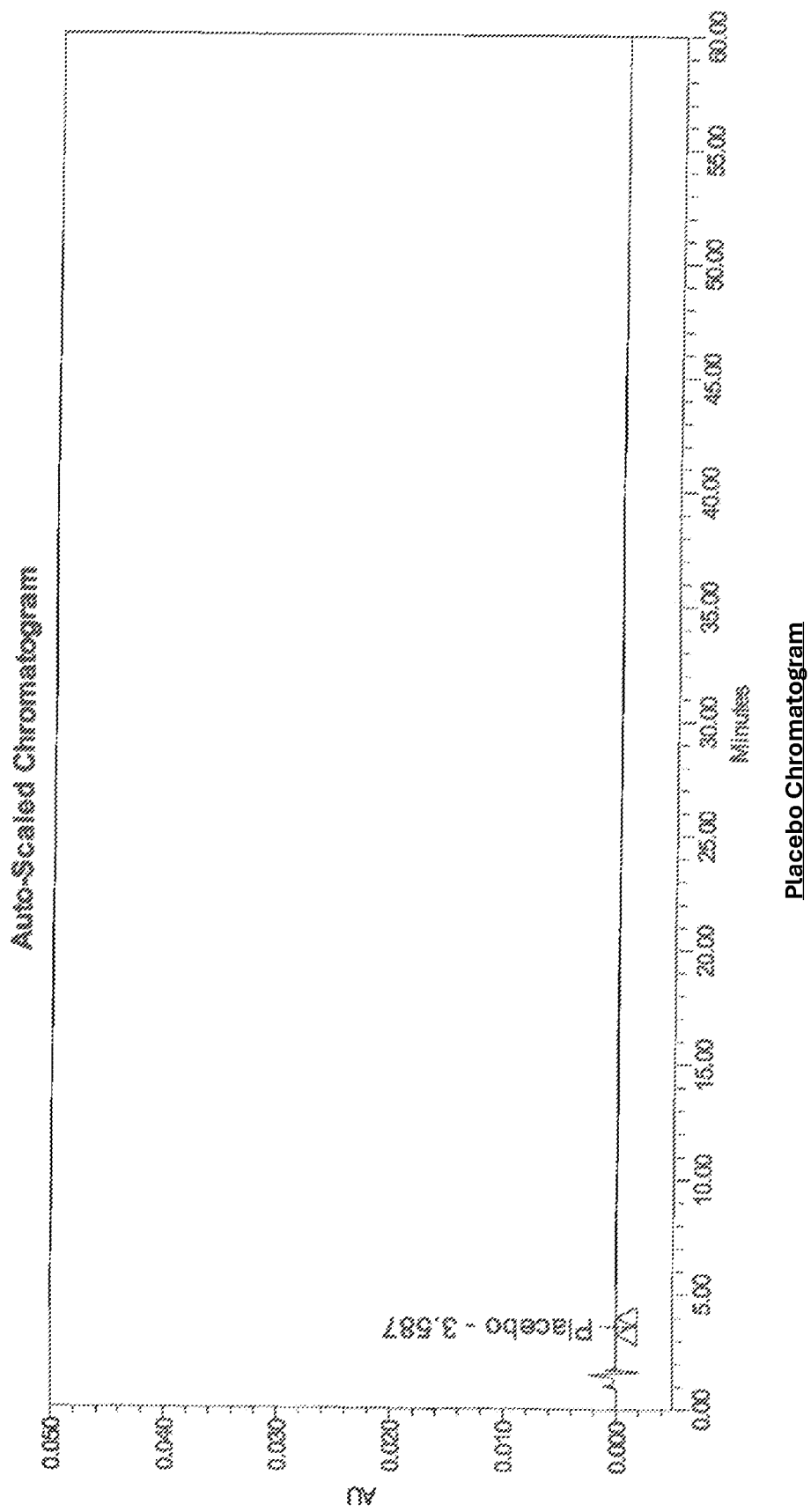
FIG. 2 shows a Placebo Chromatogram in Assay method, which is a HPLC chromatogram of placebo (not the active diltiazem drug) in solvent.

A single injection of the Placebo solution (drug product without Diltiazem) in Assay method was performed, where no peaks that interfered with Diltiazem at around 14 minutes as shown in FIG. 2.

Figure 3:
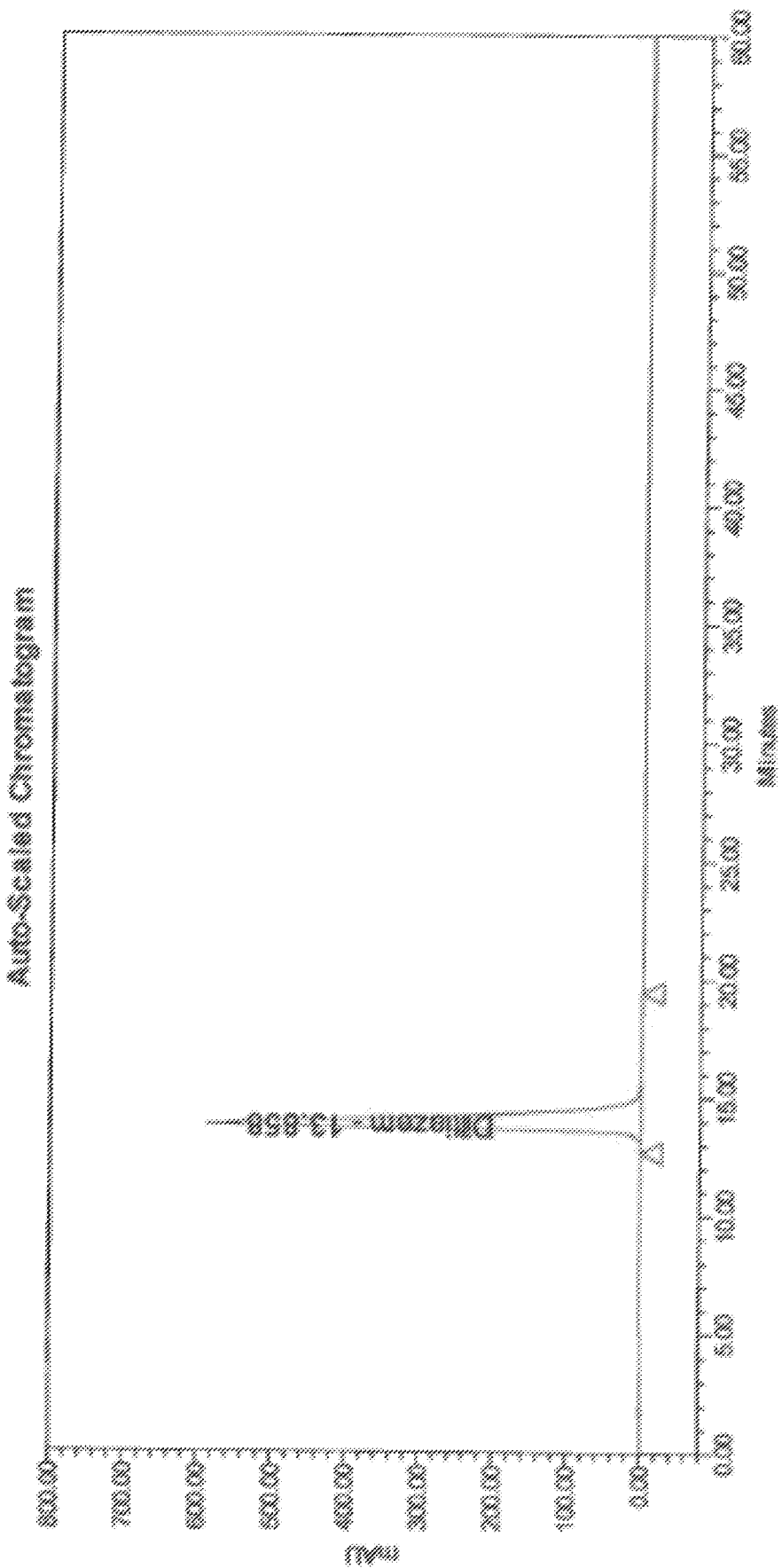
FIG. 3 shows a HPLC chromatogram of a 1000 parts per million (ppm) standard solution containing the active drug, diltiazem for Assay determination, exhibiting a peak at around 14 minutes.

A single injection of the 1000 parts per million (ppm) standard solution containing the active drug, diltiazem for Assay determination was then made. The reference chromatogram of Diltiazem at around 14 minutes is shown in FIG. 3.

Figure 4:
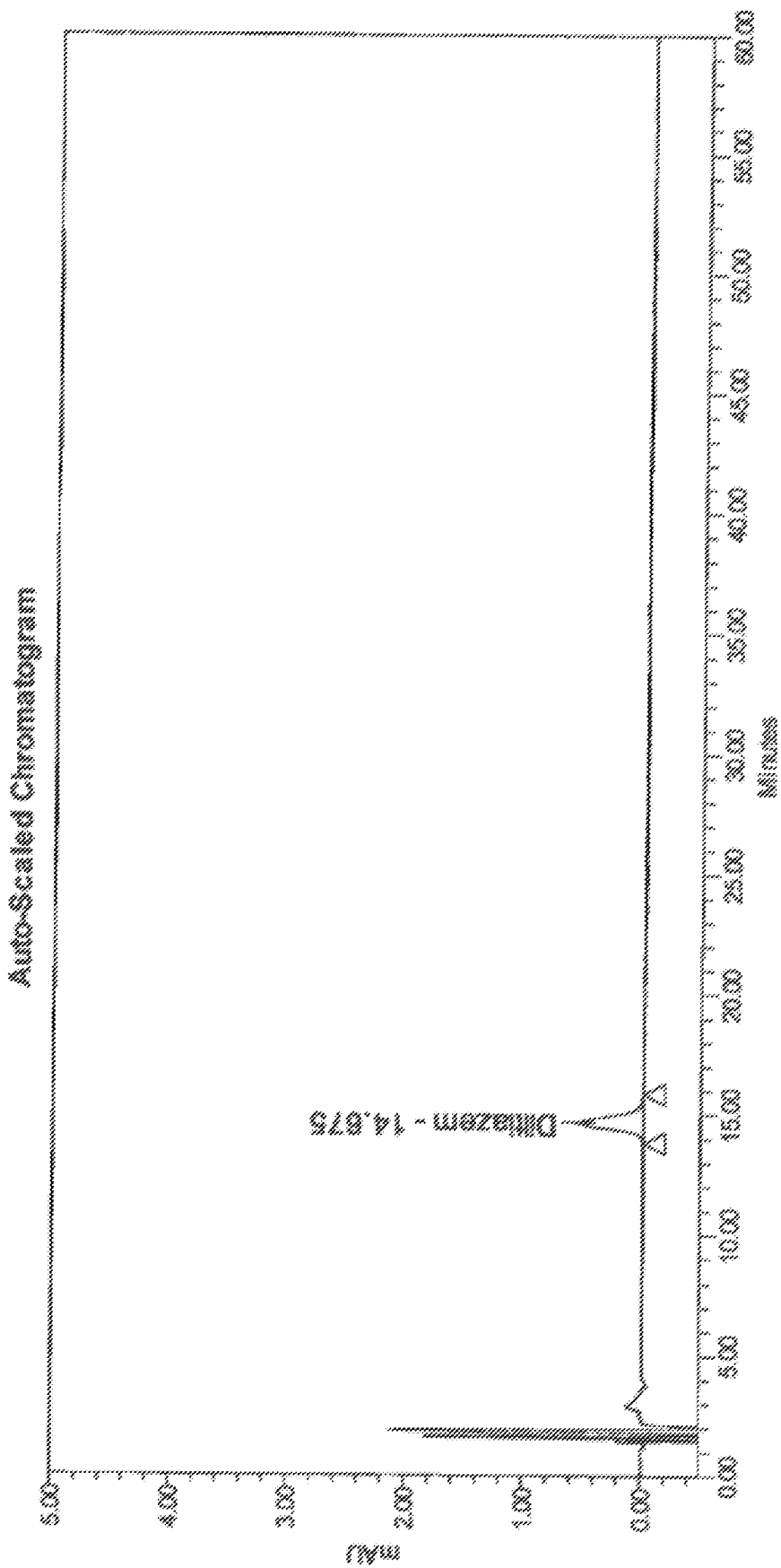
FIG. 4 shows a HPLC chromatogram of a 1 part per million (ppm) standard solution containing the active drug, diltiazem for Related substance determination, exhibiting a peak at around 14 minutes.

A single injection of 1 part per million (ppm) standard solution containing the active drug, diltiazem for related substance determination is shown in FIG. 4.

Figure 5:
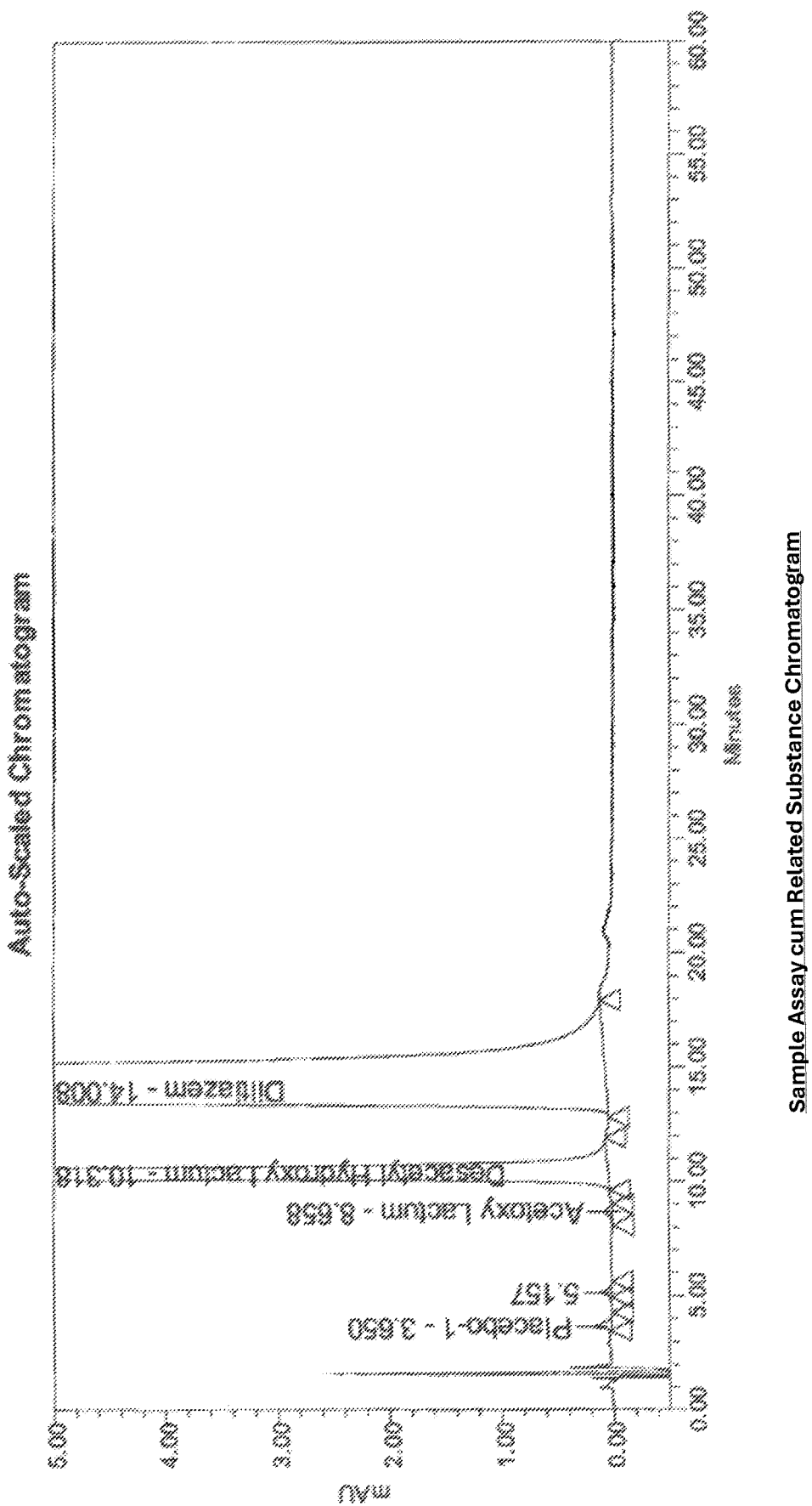
FIG. 5 shows a HPLC chromatogram of a test solution containing the active drug, diltiazem, exhibiting a peak at around 14 minutes

FIG. 5 is a chromatograph of a test solution containing the active drug, diltiazem at around 14 minutes and other known and unknown impurities obtained before Diltiazem peak.

| HPLC method conditions: | |
|---|---|
| Column: | µBondapak C18, 3.9 × 300 mm, 10µ |
| Flow Rate: | 1.6 mL/min |
| Wavelength: | UV 240 nm |
| Injection Volume: | 10 µL |
| Runtime: | 60 minutes |
| Column Oven temperature: | 25° C. |
| Sample Cooler Temperature: | 25° C. |
| Buffer: | 1.16 g/L of d-10-camphorsulfonic acid in 0.1 M sodium acetate. Adjust with 0.1 N sodium hydroxide to a pH of 6.2. |
| Mobile phase: | Acetonitrile, Methanol, and Buffer (27:25:48) |

Extensive stability testing has been conducted on a packaged, ready-to-inject diltiazem composition of the invention. The solutions were stored at refrigeration temperature and under accelerated conditions, i.e., at elevated temperatures. Stability data are presented in the Examples, herein below.

EXAMPLES

Marketed Product (Reference Standard Product) Results:
Diltiazem Hydrochloride Injection, 5 mg/ml (concentrated solution)
Mfg by: ATHENEX PHARMACEUTICAL DIVISION, LLC.
Lot No: E002A018
Exp Date: Jun-24
Storage Condition: 2 to 8° C.

The marketed product as described above was also tested as such (without dilution), and the marketed product further dilution up to 1 mg/ml with 0.9% Sodium Chloride solution and stored at 25° C./40% RH) for 3 months. The results are shown in TABLE 2, below:

TABLE 2

| CONDITION | Analyzed on 13 Nov. 2023 | Marketed product after dilution up to 1 mg/ml with 0.9% Sodium Chloride solution. (After 3 months at 25° C./40% RH) |
|---|---|---|
| DESCRIPTION | Clear, Colorless Liquid | Clear, Colorless Liquid |
| pH | 4.03 | 4.12 |
| Density | 1.0172 | — |
| ASSAY OF DILTIAZEM | 102.9 | 94.5 |
| Cis-Hydroxy Lactum | 0.00 | 0.00 |
| Acetoxy Lactum | 0.05 | 0.00 |
| Desacetyl Lactum | 2.55 | 5.12 |
| Single Max Impurity | 0.01 | 0.02 |
| TOTAL IMPURITIES | 2.61 | 5.20 |

Based on the above marketed product (concentrated formulation) data, indicate even at recommended storage refrigerated condition, before 8 months of expiry, the level of Desacetyl Lactum is around 2.5%. Apart from that after dilution and storage at 25° C./40% RH) for 3 months the level of Desacetyl Lactum is increased to double (5.12%).

Trials with different buffer systems:

The following Table 3 shows certain compositions of the invention and properties exhibited by those compositions of the invention with different buffer systems.

TABLE 3

| Ingredients | A Concentration (mg/mL) | B Concentration (mg/mL) | C Concentration (mg/mL) |
|---|---|---|---|
| Diltiazem HCl | 1 mg/ml | 1 mg/ml | 1 mg/ml |
| Citric acid Monohydrate USP | 0.15 mg/ml | — | — |
| Tri-Sodium Citrate Dihydrate USP | 0.12 mg/ml | — | — |
| Sodium Acetate Trihydrate | — | 0.012 mg/ml | 0.020 mg/mL |
| Acetic Acid | — | q.s. to adjust pH | q.s. to adjust pH |
| Sodium Chloride | 9.0 mg/mL | 9.0 mg/mL | 9.0 mg/mL |
| Water for Injection | q.s. to 1 mL | q.s. to 1 mL | q.s. to 1 mL |

Comparative analysis was conducted on a diltiazem composition prepared as described above, and tested for pH, osmolality, concentration of diltiazem, and known degradation products or impurities. The initial condition results of the stability testing are shown in TABLE 4, below:

TABLE 4

| CONDITION | A | B | C |
|---|---|---|---|
| DESCRIPTION | Clear, Colorless Liquid | Clear, Colorless Liquid | Clear, Colorless Liquid |
| pH | 3.91 | 3.97 | 4.08 |
| OSMOLALITY | 294 | 294 | 295 |
| ASSAY OF DILTIAZEM | 100.8 | 107.3 | 99.7 |
| Cis-Hydroxy Lactum | 0.00 | 0.00 | 0.00 |
| Acetoxy Lactum | 0.04 | 0.03 | 0.03 |
| Desacetyl Lactum | 0.05 | 0.06 | 0.05 |
| Single Max Impurity | 0.00 | 0.02 | 0.02 |
| TOTAL IMPURITIES | 0.09 | 0.11 | 0.11 |

The following examples describe certain compositions of the invention and properties exhibited by those compositions of the invention. These examples illustrate certain embodiments within the scope of the invention but should not be construed to limit the scope of the claims in any way.

A composition of the invention comprises the ingredients shown in Table 5, below:

TABLE 5

| Ingredients | Concentration (mg/mL) | Batch Quantity/ 2000 mL |
|---|---|---|
| Diltiazem HCl | 1 mg/ml | 2.0 g |
| Citric acid Monohydrate USP | 0.15 mg/ml | 0.3 g |
| Tri-Sodium Citrate Dihydrate USP | 0.12 mg/ml | 0.24 g |
| Sodium Chloride | 9.0 mg/mL | 18.0 g |
| Water for Injection | q.s. to 1 mL | q.s. to 2000 mL |

Preparation Procedure:

Transfer 95% (of batch size) water into a suitable container. Add Sodium Chloride, Tri-Sodium Citrate Dihydrate USP, Citric acid Monohydrate USP and mix well. Transfer Diltiazem HCl into the above solution and dissolved until a clear solution is obtained. Adjust pH, if necessary, with Hydrochloric Acid NF or Sodium hydroxide NF to a pH of about 3.9. Make up the volume to 100% by adding water. Filter the bulk solution using 0.22-micron Filter and pack in IV flexible containers.

Six-month and 15 months stability testing, under refrigerated (long-term) conditions and at accelerated conditions—room temperature at 40% relative humidity (RH), was conducted on a diltiazem composition prepared as described above, and tested for pH, osmolality, concentration of diltiazem, and known degradation products or impurities. The results of the stability testing are shown in TABLE 6, below:

TABLE 6

| | | 6 months stability | | 15 months stability | |
|---|---|---|---|---|---|
| CONDITION | Initial | 2-8° C. (Long term storage condition) | 25° C./40% RH (Accelerated storage condition) | 2-8° C. (Long term storage condition) | 25° C./40% RH (Accelerated storage condition) |
| DESCRIPTION | Clear, Colorless Liquid | Clear, Colorless Liquid | Clear, Colorless Liquid | Clear, Colorless Liquid | Clear, Colorless Liquid |
| pH | 3.91 | 3.91 | 3.89 | 3.89 | 3.88 |
| OSMOLALITY | 294 | 294 | 294 | 293 | 291 |
| ASSAY OF DILTIAZEM | 100.8 | 99.5 | 90.4 | 98.1 | 84.3 |
| Cis-Hydroxy Lactum | 0.00 | 0.01 | 0.03 | 0.00 | 0.00 |
| Acetoxy Lactum | 0.04 | 0.00 | 0.00 | 0.01 | 0.01 |
| Desacetyl Lactum | 0.05 | 0.99 | 7.28 | 2.38 | 17.49 |
| Single Max Impurity | ND | 0.01 | 0.01 | 0.01 | 0.04 |
| TOTAL IMPURITIES | 0.09 | 1.01 | 7.33 | 2.39 | 17.55 |

A second batch of a diltiazem composition prepared as described above was also tested, and the results are shown in TABLE 7, below:

TABLE 7

| CONDITION | Initial | 1M, 2-8° C. | 1M, 25° C./ 40% RH | 4.5M, 2-8° C. | 4.5M, 25° C./ 40% RH | 6M, 2-8° C. | 6M, 25° C./ 40% RH |
|---|---|---|---|---|---|---|---|
| DESCRIPTION | Clear, Colorless Liquid | Clear, Colorless Liquid | Clear, Colorless Liquid | Clear, Colorless Liquid | Clear, Colorless Liquid | Clear, Colorless Liquid | Clear, Colorless Liquid |
| pH | 3.83 | 3.83 | 3.89 | 3.93 | 3.89 | 3.90 | 3.88 |
| Density | 1.0056 | 1.0054 | 1.0036 | — | — | — | — |
| OSMOLALITY | 296 | 294 | 295 | 294 | 294 | 293 | 293 |
| ASSAY OF DILTIAZEM | 99.9 | 99.9 | 98.5 | 102.1 | 98.9 | 99.9 | 92.4 |
| Cis-Hydroxy Lactum | 0.01 | 0.00 | 0.01 | 0.01 | 0.01 | 0.01 | 0.01 |
| Acetoxy Lactum | 0.03 | 0.03 | 0.03 | 0.00 | 0.00 | 0.00 | 0.00 |
| Desacetyl Lactum | 0.26 | 0.26 | 1.48 | 0.82 | 4.24 | 1.02 | 6.83 |
| Single Max Impurity | 0.02 | 0.02 | 0.01 | 0.01 | 0.02 | 0.02 | 0.02 |
| TOTAL IMPURITIES | 0.32 | 0.32 | 1.53 | 0.84 | 4.27 | 1.05 | 6.86 |

Regular testing was performed to measure key chemical stability parameters including:
Diltiazem potency
Degradants and impurities
Physical appearance, and
pH.

The optimal target thresholds included diltiazem potency remaining at 90% or greater of the initial concentration, minimal to undetectable degradants, maintenance of clear and colorless appearance, and impurities within acceptance limit. Solutions remained clear without precipitation or significant color changes. The data indicates aseptic filling provides optimal shelf life of 24 months for the proposed refrigeration temperature stable Diltiazem formulations.

Limits of ≤5.0% applied to the desacetyl diltiazem HCL degradant based on this physiologically active substance being one of the two principal human metabolites [as per Molden E, et al. Desacetyl-diltiazem displays severalfold higher affinity to CYP2D6 compared with CYP3A4. *Drug Metab Dispos.* 30: 1-3 (2002)].

There are no safety issues with an expiry limit of ≤5.0% as per literature-based toxicology evaluation.

In summary, the stability testing for a composition of the subject invention provides substantial evidence that the disclosed diltiazem IV solutions can retain adequate potency, purity, and quality for 6-24 months when stored at refrigeration temperature conditions. This meets the target criteria established at the outset of developing shelf-stable ready-to-inject Diltiazem formulations that avoid the need for on-site dilution prior to patient administration. The novel compositions and packaging achieve the goals of enhanced convenience, accuracy, and safety compared to currently available Diltiazem products.

The above disclosure and example generally describe the present invention and is provided for purposes of illustration and is not intended to limit the scope of the invention. The invention described herein may be practiced in the absence of any element or elements, limitation or limitations which is not specifically disclosed herein. Thus, for example, in each instance herein, any of the terms "comprising," "consisting essentially of," and "consisting of" may be replaced with either of the other two terms. The terms and expressions are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

The invention claimed is:

1. A stable, isotonic injectable diltiazem composition, said composition consisting of:
   about 0.5-1.5 mg/mL diltiazem HCL as an active pharmaceutical ingredient; and
   about 0.4 mg/mL or less of a buffer for maintenance of pH, said buffer selected from the group consisting of: (a) about 0.15 mg/mL citric acid monohydrate and about 0.12 mg/mL tri-sodium citrate dihydrate, and (b) about 0.01 to 0.02 mg/mL sodium acetate trihydrate and acetic acid; and
   a pharmaceutically acceptable salt as a tonicity agent; and
   water for injection;
   wherein the composition has a pH of about 2.5 to about 5.0.

2. The composition of claim 1, wherein the pharmaceutically acceptable salt as a tonicity agent is sodium chloride.

3. The composition of claim 2, wherein the composition comprises up to 1% sodium chloride.

4. The composition of claim 1, wherein the composition is stable for at least one month at room temperature.

5. The composition of claim 1, wherein the composition is stable for six to 24 months under refrigerated conditions.

6. The composition of claim 1, wherein the composition is stable when assayed desacetyl diltiazem HCL degradant is ≤5.0%.

7. The composition of claim 1, wherein the composition is stable when assayed total degradants and impurities are ≤5.0%.

8. The composition of claim 1, wherein the diltiazem is at least 95% of the original amount up to 1 month when stored at room temperature.

9. The composition of claim 1, wherein the diltiazem is at least 95% of the original amount up to six months when stored under refrigerated conditions.

10. The composition of claim 1, wherein the diltiazem is at least 90% of the original amount up to 12 months when stored under refrigerated conditions.

11. The composition of claim 1, wherein the pH range is about 3.4 to about 4.4.

12. The composition of claim 1, wherein the pH is about 3.9.

* * * * *